United States Patent [19]

Burrell et al.

[11] Patent Number: 5,770,255

[45] Date of Patent: *Jun. 23, 1998

[54] ANTI-MICROBIAL COATING FOR MEDICAL DEVICES

[75] Inventors: Robert E. Burrell, Sherwood Park; Larry Roy Morris, Edmonton, both of Canada

[73] Assignee: Westaim Technologies, Inc., Alberta, Canada

[ * ] Notice: The term of this patent shall not extend beyond the expiration date of Pat. No. 5,454,886.

[21] Appl. No.: 128,027

[22] Filed: Sep. 29, 1993

Related U.S. Application Data

[63] Continuation of Ser. No. 885,758, May 19, 1992, abandoned.

[51] Int. Cl.$^6$ .............................. B05D 7/00; A61L 29/00; A61L 27/00

[52] U.S. Cl. ........................ 427/2.1; 427/2.12; 427/2.25; 427/2.3; 427/250; 427/526; 427/593; 204/192.1; 204/192.14

[58] Field of Search .................................... 427/2.1, 2.12, 427/2.25, 2.28, 2.3, 2.31, 250, 526, 593; 204/192.1, 192.14, 192.31; 623/11; 604/19

[56] References Cited

U.S. PATENT DOCUMENTS

| | | |
|---|---|---|
| 2,103,999 | 12/1937 | Muller et al. . |
| 2,785,153 | 3/1957 | Locke et al. . |
| 4,043,932 | 8/1977 | Fresenius et al. ...................... 424/610 |
| 4,054,139 | 10/1977 | Crossley . |
| 4,167,045 | 9/1979 | Sawyer ........................................ 3/1.4 |
| 4,325,776 | 4/1982 | Menzel . |
| 4,341,569 | 7/1982 | Yaron et al. . |
| 4,377,675 | 3/1983 | Daudt et al. .............................. 528/25 |
| 4,404,233 | 9/1983 | Ikeda et al. ............................. 427/526 |
| 4,411,041 | 10/1983 | Braga . |
| 4,411,648 | 10/1983 | Davis et al. . |

(List continued on next page.)

FOREIGN PATENT DOCUMENTS

| | | |
|---|---|---|
| 1106718 | 8/1981 | Canada . |
| 2033107 | 6/1992 | Canada . |
| 206024 | 6/1985 | European Pat. Off. . |
| 0 206 024 | 12/1986 | European Pat. Off. . |
| 0 254 413 | 1/1988 | European Pat. Off. . |
| A 0 415 206 A2 | 3/1991 | European Pat. Off. . |
| 0 488 269 | 6/1992 | European Pat. Off. . |
| 819 131 | 12/1948 | Germany . |
| 3302567 | 7/1984 | Germany . |
| 3830359 | 12/1989 | Germany . |
| 90 17 361.9 | 3/1991 | Germany . |
| 57-500588 | 4/1982 | Japan . |
| 60-21912 | 2/1985 | Japan . |
| 62-56018 | 4/1987 | Japan . |
| 2 073 024 | 10/1981 | United Kingdom . |
| 2 134 791 | 8/1984 | United Kingdom . |
| PCT/US92/ 08266 | 4/1993 | WIPO . |

OTHER PUBLICATIONS

Spadaro, J.A., et al, 1979. "Silver Polymethyl Methacrylate Antibacterial Bone Cement" Clinical Orthopaedics and Related Research, No. 143, Sep. 1979, pp. 266–270.

Becker, R.O., et al., 1978. "Treatment of Orthopaedic Infections with Electrically Generated Silver Ions" The Journal of Bone and Joint Surgery, vol. 60–A, No. 7, Oct. 1978, pp. 871–881.

Research & Development Magazine, Oct. 1993, Consumer Products "SILDATE" p. 41.

Gleiter, H., 1992. "Materials With Ultrafine Microstructures: Retrospective and Perspectives" NanoStructured Materials, vol. 1, pp. 1–19. (no month).

Birringer, R., et al., 1986. "Nanocrystalline Materials—A First Report" Grain Boundary Structure and Related Phenomena Proceedings of JIMIS–4 (1986). Supplement to Transactions of the Japan Institute of Metals pp. 43–52 (no month).

H.E. Morton, "Pseudomonas," in *Antiseptics and Disinfectants*, 401–411 (S.S. Block, Lea, and Febiger ed. 1977). (no month).

N. Grier, "Silver and Its Compounds," in *Antiseptics and Disinfectants*, 375–389 (S.S. Block, Lea and Febiger ed. 1977). (no month).

E. Deitch et al., "Silver–Nylon: A New Antimicrobial Agent," Antimicrobial Agents and Chemotherapy, vol. 23 (3):356–359 (Mar. 1983).

P. MacKeen et al., "Silver–Coated Nylon Fiber as an Antibacterial Agent," Antimicrobial Agents and Chemotherapy, vol. 31 (1):93–99 (Jan. 1987).

A. Marino et al., "Electrical Augmentation of the Antimicrobial Activity of Silver–Nylon Fabrics," Journal of Biological Physics, vol. 12: 93–98 (1984). (no month).

M. Tanemura et al., "Growth of microprojections arising from sputter etching of Cu–Ag sandwich," J. Vac. Sci. Technol. A., vol. 4, (5): 2369–2372 (Sep./Oct. 1986).

R. Bunshah, "Deposition Technologies: An Overview," in *Deposition Technologies for Films and Coatings*, Noyes Publications, N.J., 1–18 (1982). (no month).

J. Thornton, "Influence of apparatus geometry and deposition conditions on the structure and topography of thick sputtered coatings," J. Vac. Sci. Technol., vol. 11, (4):666–670 (Jul./Aug. 1974).

(List continued on next page.)

*Primary Examiner*—Diana Dudash
*Attorney, Agent, or Firm*—Finnegan, Henderson, Farabow, Garrett & Dunner, L.L.P.

[57] ABSTRACT

Anti-microbial coatings and method of forming same on medical devices. The coatings are formed by depositing a biocompatible metal by physical vapor deposition techniques to produce atomic disorder in the coating such that a sustained release of metal ions sufficient to produce an anti-microbial effect is achieved. Preferred deposition conditions to achieve atomic disorder include a lower than normal substrate temperature, and one or more of a higher than normal working gas pressure and a lower than normal angle of incidence of coating flux.

21 Claims, No Drawings

U.S. PATENT DOCUMENTS

| | | |
|---|---|---|
| 4,418,686 | 12/1983 | Child . |
| 4,443,488 | 4/1984 | Little et al. . |
| 4,476,590 | 10/1984 | Scales et al. . |
| 4,483,688 | 11/1984 | Akiyama . |
| 4,520,039 | 5/1985 | Ovshinsky . |
| 4,528,208 | 7/1985 | Hirvonen et al. .................. 427/526 |
| 4,543,275 | 9/1985 | Akashi et al. ..................... 427/526 |
| 4,564,361 | 1/1986 | Akiyama . |
| 4,569,673 | 2/1986 | Tesi . |
| 4,590,031 | 5/1986 | Eichen et al. ................. 204/192.15 |
| 4,592,920 | 6/1986 | Murtfeldt . |
| 4,603,152 | 7/1986 | Laurin et al. . |
| 4,612,337 | 9/1986 | Fox, Jr. et al. . |
| 4,615,705 | 10/1986 | Scales et al. . |
| 4,642,104 | 2/1987 | Sakamoto et al. . |
| 4,657,772 | 4/1987 | Kocak . |
| 4,664,960 | 5/1987 | Ovshinsky . |
| 4,670,292 | 6/1987 | Fujita et al. . |
| 4,677,143 | 6/1987 | Laurin et al. . |
| 4,683,149 | 7/1987 | Suzuki et al. .................. 427/255.7 |
| 4,693,760 | 9/1987 | Sioshansi . |
| 4,716,083 | 12/1987 | Eichen et al. ................. 204/192.15 |
| 4,718,905 | 1/1988 | Freeman . |
| 4,743,308 | 5/1988 | Sioshansi et al. . |
| 4,743,493 | 5/1988 | Sioshansi et al. . |
| 4,846,834 | 7/1989 | von Recum et al. ................ 623/11 |
| 4,849,223 | 7/1989 | Pratt et al. . |
| 4,855,026 | 8/1989 | Sioshansi . |
| 4,867,968 | 9/1989 | Allen . |
| 4,886,505 | 12/1989 | Haynes et al. . |
| 4,902,503 | 2/1990 | Umemura et al. . |
| 4,906,466 | 3/1990 | Edwards et al. .................... 424/78 |
| 4,923,450 | 5/1990 | Maeda et al. . |
| 4,932,948 | 6/1990 | Kernes et al. . |
| 4,933,178 | 6/1990 | Capelli . |
| 4,944,961 | 7/1990 | Lu et al. . |
| 4,952,419 | 8/1990 | De Leon et al. .................. 427/202 |
| 4,960,415 | 10/1990 | Reinmuller . |
| 4,973,320 | 11/1990 | Brenner et al. . |
| 5,005,518 | 4/1991 | Yamada ............................ 118/716 |
| 5,019,096 | 5/1991 | Fox, Jr. et al. . |
| 5,019,601 | 5/1991 | Allen . |
| 5,045,318 | 9/1991 | Tengvall et al. . |
| 5,047,385 | 9/1991 | Beasley et al. . |
| 5,049,140 | 9/1991 | Brenner et al. . |
| 5,055,169 | 10/1991 | Hock, Jr. et al. .................. 427/531 |
| 5,057,106 | 10/1991 | Kasevich et al. ................... 606/33 |
| 5,073,382 | 12/1991 | Antelman . |
| 5,078,902 | 1/1992 | Antelman . |
| 5,080,671 | 1/1992 | Oron et al. . |
| 5,089,275 | 2/1992 | Antelman . |
| 5,098,434 | 3/1992 | Serbousek . |
| 5,098,582 | 3/1992 | Antelman . |
| 5,108,399 | 4/1992 | Eitenmuller et al. . |
| 5,123,924 | 6/1992 | Sioshansi et al. . |
| 5,123,927 | 6/1992 | Duncan et al. . |
| 5,133,757 | 7/1992 | Sioshansi et al. . |
| 5,152,774 | 10/1992 | Schroeder ....................... 427/2.28 |
| 5,152,783 | 10/1992 | Suzuki et al. ................... 427/2.28 |
| 5,152,993 | 10/1992 | Bjursten et al. . |
| 5,180,585 | 1/1993 | Jacobson et al. .................. 424/405 |
| 5,207,706 | 5/1993 | Menaker ............................ 623/1 |
| 5,211,855 | 5/1993 | Antelman . |
| 5,223,149 | 6/1993 | Antelman . |
| 5,242,706 | 9/1993 | Cotell et al. .................... 427/2.27 |
| 5,322,520 | 6/1994 | Milder . |
| 5,405,644 | 4/1995 | Ohsumi et al. ................... 427/2.31 |
| 5,427,631 | 6/1995 | Johansson et al. ................ 148/23.8 |
| 5,454,886 | 10/1995 | Burrell et al. .................... 148/565 |
| 5,468,562 | 11/1995 | Farivar et al. .................... 428/457 |
| 5,474,797 | 12/1995 | Sioshansi et al. ................... 427/2.3 |
| 5,520,664 | 5/1996 | Bricault, Jr. et al. .................. 604/265 |

OTHER PUBLICATIONS

R.P. Andres et al., "Research opportunities on clusters and cluster–assembled materials—A Department of Energy, Council on Materials Science Panel Report," J. Mater. Res., vol. 4, (3): 704–736 (May/Jun. 1989).

J. Nickel et al., "Antibiotic Resistance of *Pseudomonus aeruginosa* Colonizing a Urinary Catheter in Vivo," Eur. J. Clin. Microbiol, vol. 4 (2):213–218 (Apr. 1985).

Product Brochures; SPI–ARGENT no date available.

P. Sioshansi, "Surface Coatings by Ion Beam Assisted Deposition," presented at Thin Films '91, San Diego, Calif., Sep. 26 & 27, 1991.

Letter and enclosures dated Dec. 16, 1991, from John E. Barry (Spire Corporation) to Applicant, Dr. Burrell.

Announcement by Spire Corp. in *New Coatings and Surfaces*, Sep. 1991.

S. Barranco et al., "In Vitro Effect of Weak Direct Current on Staphylococcus Aureus," Clinical Orthopaedics and Related Research, No. 100, 250–255 (May 1974).

J. Spadaro et al., "Antibacterial Effects of Silver Electrodes with Weak Direct Current," Antimicrobial Agents and Chemotherapy, vol. 6 (5):637–642 (Nov. 1974).

J. Spadaro et al., "Some Specific Cellular Effects of Electrically Injected Silver and Gold Ions," Bioelectrochem. and Bioenergetics, No. 3, 49–57 (1976). (no month).

T. Berger et al., "Electrically Generated Silver Ions: Quantitative Effects on Bacterial and Mammalian Cells," Antimicrobial Agents and Chemotherapy, 357–358 (Feb. 1976).

T. Berger et al., "Antifungal Properties of Electrically Generated Metallic Ions," Antimicrobial Agents and Chemotherapy, vol. 10 (5): 856–860 (Nov. 1976).

J. Spadaro, "Antibacterial Effects of Silver Electrodes," Eng. in Med. & Biol. Soc., 215–218 (1981). (no month).

D. Webster et al., "Silver Anode Treatment of Chronic Osteomyelitis," Clinical Orthopaedics and Related Research, No. 161, 105–114 (Nov./Dec. 1981).

C. Davis et al., "Iontophoretic Killing of *Escherichia coli* in Static Fluid and in a Model Catheter System," Journal of Clinical Microbiology, vol. 15 (5): 891–894 (May 1982).

J. Spadaro et al., "Antibacterial Fixation Pins With Silver: Animal Models," J. Biol. Phys., No. 12 (1984). (no month).

A. Marino et al., "Electrochemical Properties of Silver–Nylon Fabrics," J. Electrochem. Soc., vol. 132 (1):68–72 (Jan. 1985).

J. Spadaro, "Bone Formation and Bacterial Inhibition with Silver and Other Electrodes," Reconstr. Surg. Traumat., vol. 19, 40–50 (1985). (no month).

A. Falcone et al., "Inhibitory Effects of Electrically Activated Silver Material on Cutaneous Wound Bacteria," Plastic and Reconstructuve Surgery, 455–459 (Mar. 1986).

J. Spadaro et al., "Bacterial inhibition by electrical activation of percutaneous silver implants," Journal of Biomedical Materials Research, vol. 20, 565–577 (1986). (no month).

R.E. Hall et al., "Inhibitory and Cidal Antimicrobial Actions of Electrically Generated Silver Ions," J. Oral Maxillofac. Surg., No. 45, 779–784 (1987). (no month).

C.P. Davis et al., "Effects of Microamperage, Medium, and Bacterial Concentration of Iontophoretic Killing of Bacteria in Fluid," Antimicrobial Agents and Chemotherapy, vol. 33 (4): 442–447 (Apr. 1989).

R. Kirchheim et al., "Free Energy of Active Atoms in Grain Boundaries of Nanocrystalline Copper, Nickel and Palladium," NanoSTRUCTURED MATERIALS, vol. 1, 167–172 (1992). (no month).

E. Deitch et al., "Silver Nylon Cloth: In vitro and in vivo Evaluation of Antimicrobial Activity," Journal of Trauma, vol. 27 (3): 301–304 (1987). (no month).

J. Thornton, "Coating Deposition by Sputtering," in *Deposition Technologies For Films and Coatings*, Noyes Publications, N.J. 170–237 (1982). (no month).

M. Lardon et al., "Influence of the substrate temperature and the discharge voltage on the structure of titanium films produced by ion–plating," Vacuum, vol. 30 (7):255–260 (1980). (no month).

F. Froes et al., "Nanocrystalline Metals for Structural Applications," JOM, vol. 41 (6):12–17 (Jun. 1989).

W. Schlump et al., Nanocrystalline materials by mechanical alloying, Technische Mitteilungen Krupp, No. 2, 69–76 (Nov. 1989).

Colmano, G., et al. 1980. "Activation of Antibacterial Silver Coatings on Surgical Implants by Direct Current: Preliminary Studies in Rabbits", Am.J.Vet.Res., vol. 41, No. 6, 1980, pp. 964–966. (no month).

Spadaro, J.A., et al. 1983. "Direct Current Activation of Bacteriostatic Silver Electrodes—1983 abstract—Transactions of the Bioelectric Repair and Growth Society", vol. 3, pp. 37. (no month).

Spadaro, J.A., et al. 1981. "Electrical Activation of Silver Bacteriostasis—Transactions of Society For Biomaterials", vol. 4, p. 70, 1981.—presented at the 7th Annual Meeting Society for Biomaterials, Troy New York, May 29, 1981.

ANTI-MICROBIAL COATING FOR MEDICAL DEVICES

This is a continuation of application Ser. No. 07/885,758, filed May 19, 1992, which is hereby incorporated by reference, now abandoned.

FIELD OF THE INVENTION

This invention relates to methods of forming anti-microbial coatings on medical devices and medical devices formed thereby. More particularly, the invention relates to coatings of biocompatible metals which provide a sustained release of anti-microbial metal ions when in contact with body fluids or body tissues.

BACKGROUND OF THE INVENTION

The need for an effective anti-microbial coating is well established in the medical community. Physicians and surgeons using medical devices and appliances ranging from orthopaedic pins, plates and implants through to wound dressings and urinary catheters must constantly guard against infection. An inexpensive anti-microbial coating also finds application in medical devices used in consumer healthcare and personal hygiene products as well as in biomedical/biotechnical laboratory equipment. The term "medical device", as used herein and in the claims is mean to extend to all such products.

The anti-microbial effects of metallic ions such as Ag, Au, Pt, Pd, Hg (i.e. the noble metals), Cu, Sn, Sb, Bi and Zn are known (see Morton, H. E., Pseudomonas in Disinfection, Sterilization and Preservation, ed. S. S. Block, Lea and Febiger, 1977 and Grier, N., Silver and Its Compounds in Disinfection, Sterilization and Preservation, ed. S. S. Block, Lea and Febiger, 1977). Of the metallic ions with anti-microbial properties, silver is perhaps the best known due to its unusually good bioactivity at low concentrations. This phenomena is termed oligodynamic action. In modern medical practice both inorganic and organic soluble salts of silver are used to prevent and treat microbial infections. While these compounds are effective as soluble salts, they do not provide prolonged protection due to loss through removal or complexation of the free silver ions. They must be reapplied at frequent intervals to overcome this problem. Reapplication is not always practical, especially where an in-dwelling or implanted medical device is involved.

Attempts have been made to slow down the release of silver ions during treatment by creating silver containing complexes which have a lower level of solubility. For example, U.S. Pat. No. 2,785,153 discloses colloidal silver protein for this purpose. Such compounds are usually formulated as creams. These compounds have not found wide applicability in the medical area due to their limited efficacy. The silver ion release rate is very slow. Furthermore, coatings from such compounds have been limited due to adhesion, abrasion resistance and shelf life problems.

The use of silver metal coatings for anti-microbial purposes has been suggested. For instance, see Deitch et al., Antimicrobial Agents and Chemotherapy, Vol. 23(3), 1983, pp. 356–359 and Mackeen et al., Antimicrobial Agents and Chemotherapy, Vol. 31(1), 1987, pp. 93–99. However, it is generally accepted that such coatings alone do not provide the required level of efficacy, since diffusion of silver ions from a metallic surface is negligible.

Given the failure of metallic silver coatings to generate the required efficacy, other researchers have tried novel activation processes. One technique is to use electrical activation of metallic silver implants (see Spadaro et al., Journal of Biological Physics, Vol. 12, 1984, pp. 93–98). Electrical stimulation of metallic silver is not always practical, especially for mobile patients. Attempts to overcome this problem include developing in situ electrical currents through galvanic action. Metal bands or layers of different metals are deposited on a device as thin film coatings. A galvanic cell is created when two metals in contact with each other are placed in an electrically conducting fluid. One metal layer acts as an anode, which dissolves into the electrolyte. The second metal acts as a cathode to drive the electrochemical cell. For example, in the case of alternating layers of Cu and Ag, the Cu is the anode, releasing $Cu^+$ ions into the electrolyte. The more noble of the metals, Ag, acts as the cathode, which does no ionize and does not go into solution to any large extent. An exemplary device of this nature is described in U.S. Pat. No. 4,886,505 issued Dec. 12, 1989, to Haynes et al. The patent discloses sputtered coatings of two or more different metals with a switch affixed to one of the metals such that, when the switch is closed, metal ion release is achieved.

Previous work has shown that a film composed of thin laminates of alternating, different metals such as silver and copper can be made to dissolve if the surface is first etched. In this instance, the etching process creates a highly textured surface (see M. Tanemure and F. Okayama, J. Vac. Sci. Technol., 5, 1986, pp 2369–2372). However, the process of making such multilaminated films is time consuming and expensive.

Electrical activation of metallic coatings has not presented a suitable solution to the problem. It should be noted that galvanic action will occur only when an electrolyte is present and if an electrical connection between the two metals of the galvanic couple exists. Since galvanic corrosion occurs primarily at the metallic interface between the two metals, electrical contact is not sustained. Thus a continuous release of metal ions over an extended period of time is not probable. Also, galvanic action to release a metal such as silver is difficult to achieve. As indicated above, the metal ions exhibiting the greatest anti-microbial effect are the noble metals, such as Ag, Au, Pt and Pd. There are few metals more noble than these to serve as cathode materials so as to drive the release of a noble metal such as Ag at the anode.

A second approach to activating the silver metal surface is to use heat or chemicals. U.S. Pat. Nos. 4,476,590 and 4,615,705, issued to Scales et al. on Oct. 16, 1984 and Oct. 7, 1986, respectively, disclose methods of activating silver surface coatings on endoprosthetic implants to render them bioerodible by heating at greater than 180° C. or by contacting with hydrogen peroxide. Such treatments are limited in terms of the substrate/devices which can be coated and activated.

There is still a need for an efficacious, inexpensive anti-microbial coating having the following properties:

sustained release of an anti-microbial agent at therapeutically active levels;

applicable to a wide variety of devices and materials;

useful shelf life; and low mammalian toxicity.

SUMMARY OF THE INVENTION

The inventors have discovered that it is possible to form a thin film metal containing coating on substrates typically used in medical devices, which coating is capable of sustained release of metal ions at anti-microbial concentrations when in contact with an alcohol or a water based electrolyte such as body fluids or body tissue. The coating is formed by physical vapour deposition techniques such as evaporation, sputtering, magnetron sputtering and ion plating in a manner such that atomic disorder occurs in the coating. Atomic disorder, as used herein and in the claims, includes high concentrations of point defects in a crystal lattice, vacancies, line defects such as dislocations, interstisial atoms, amorphous regions, grain and sub grain boundaries and the like. Atomic disorder leads to irregularities in surface topography and inhomogeneities in the structure on the nanometer scale.

The deposition conditions preferably used to produce atomic disorder in the coating are outside the normal range of operating conditions used to produce defect free, dense, smooth films. Such normal coating practices are well known (see for example R. F. Bunshah et al., "Deposition Technologies for Films and Coatings", Noyes Publications, N.J., 1982). In general, the deposition conditions used in accordance with the present invention to produce atomic disorder such that a sustained release of metal ions sufficient to produce an antimicrobial effect is achieved, include:

a lower than normal substrate temperature; and optionally one or more of:

a higher than normal working gas pressure;

a lower than normal angle of incidence of the coating flux; and a higher than normal coating flux (rate of deposition).

The low substrate temperature is achieved by maintaining the ratio of the temperature of the surface being coated (the substrate) to the melting point of the coating metal, T/Tm, at less than about 0.5. More preferably this ratio is maintained at less than about 0.35, and most preferably at less than 0.30. In this ratio, the temperatures of the substrate and metal are in degrees Kelvin.

Normal or ambient working gas pressure for depositing the usually required dense, smooth, defect free metal films vary according to the method of physical vapour deposition being used. In general, for sputtering, the normal working gas pressure is less than 75 mT (milliTorr), for magnetron sputtering, less than 10 mT, and for ion-plating less than 200 mT. Normal ambient gas pressures vary for vacuum evaporation processes, from 0.1 mT for vacuum evaporation, to 100 mT for arc evaporation, to 200 mT for pressure plating. Thus, in accordance with the method of the present invention, in addition to using low substrate temperatures to achieve atomic disorder, working (or ambient) gas pressures higher than these normal values may be used to increase the level of atomic disorder in the coating.

Another condition discovered to have an effect on the level of atomic disorder in the coatings of the present invention is the angle of incidence of the coating flux during deposition. Normally to achieve dense, smooth coatings, this angle is maintained at about 90°+/−15°. In accordance with the present invention, in addition to using low substrate temperatures during deposition to achieve atomic disorder, angles of incidence lower than about 75° may be used to increase the level of atomic disorder in the coating.

Yet another process parameter having an effect on the level of atomic disorder is the atom flux to the surface being coated. High deposition rates tend to increase atomic disorder, (see for example R. F. Bunshah et al., "Deposition Technologies for Films and Coatings", Noyes Publications, N.J., 1982); however, high deposition rates also tend to increase the coating temperature. Thus, there is an optimum deposition rate that depends on the deposition technique, the coating material and other process parameters.

The metals used in the coating are those which have an anti-microbial effect, but which are biocompatible (non-toxic for the intended utility). Preferred metals include Ag, Au, Pt, Pd, Hg (i.e. the noble metals), Sn, Cu, Sb, Bi, and Zn or alloys of two or more of said metals. Most preferred is Ag or its alloys.

DESCRIPTION OF THE PREFERRED EMBODIMENTS

The device to be coated in accordance with the present invention is one which comes into contact with an alcohol or a water based electrolyte such as a body fluid (for example blood, urine or saliva) or body tissue (for example skin or bone) for any period of time such that microorganism growth on the device surface is possible. In most cases the devices are medical devices such as catheters, implants, tracheal tubes, orthopaedic pins, insulin pumps, would closures, drains, dressings, shunts, connectors, prosthetic devices, pacemaker leads, needles, surgical instruments, dental prostheses, ventilator tubes and the like. However, it should be understood that the invention is not limited to such devices and may extend to other devices useful in consumer healthcare, such as sterile packaging, clothing and footwear, personal hygiene products such as diapers and sanitary pads, in biomedical or biotechnical laboratory equipment, such as tables, enclosures and wall coverings, and the like. The term "medical device" as used herein and in the claims is intended to extend broadly to all such devices.

The device may be made of any suitable material, for example metals, including steel, aluminum and its alloys, latex, nylon, silicone, polyester, glass, ceramic, paper, cloth and other plastics and rubbers. For use as an in-dwelling medical device, the device will be made of a bioinert material. The device may take on any shape dictated by its utility, ranging from flat sheets to discs, rods and hollow tubes. The device may be rigid or flexible, a factor again dictated by its intended use.

The anti-microbial coating in accordance with this invention is deposited as a thin metallic film on one or more surfaces of the device by physical vapour deposition techniques. Such techniques, which are well known in the art, all deposit the metal from the vapour, generally atom by atom, onto a substrate surface. The techniques include vacuum evaporation, sputtering, magnetron sputtering and ion plating. The deposition is conducted in a manner to create atomic disorder in the coating as defined hereinabove. Various conditions responsible for producing atomic disorder are known in the art, these being the conditions which are generally avoided in thin film deposition techniques where the object is to create a defect free, smooth and dense film (see for example J. A. Thornton, Structure and Topography of Sputtered Coatings, J. Vac. Sci. Technol., 11(4), 666–670, 1974).

The preferred conditions which are used to create atomic dislocation during the deposition process include:

a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3; and optionally one or both of:

a higher than normal working (or ambient) gas pressure, i.e. for vacuum evaporation, greater than 0.1 mT, for arc evaporation greater than 100 mT, for pressure plating greater than 200 mT, for sputtering, greater than 75 mT, for magnetron sputtering, greater than about 10 mT, and for ion plating, greater than about 200 mT;

maintaining the angle of incidence of the coating flux on the surface to be coated at less than about 75°, and preferably less than about 30°.

The metals used in the coating are those known to have an anti-microbial effect. For most medical devices, the metal must also be biocompatible. Preferred metals include the noble metals Ag, Au, Pt, Pd, and Hg as well as Sn, Cu, Sb, Bi, and Zn or allows of two or more of these metals. Most preferred is Ag or Au, or alloys of one or more of these metals.

The coating is formed as a thin film on at least a part of the surface of the medical device. The film has a thickness no greater than that needed to provide a sustained release of metal ions over a suitable period of time. In that respect, the thickness will vary with the particular metal in the coating (which varies the solubility and abrasion resistance), and with the degree of atomic disorder in (and thus the solubility of) the coating. The thickness will be thin enough that the coating does not interfere with the dimensional tolerances or flexibility of the device for its intended utility. Typically, thicknesses of less than 1 micron have been found to provide sufficient sustained anti-microbial activity. Increased thicknesses may be used depending on the degree of metal ion release needed over a period of time. Thicknesses greater than 10 microns are more expensive to produce and normally should not be needed.

The anti-microbial effect of the coating is achieved when the device is brought into contact with an alcohol or a water based electrolyte such as, a body fluid or body tissue thus releasing metal ions. The concentration of the metal which is needed to produce an anti-microbial effect will vary from metal to metal. Generally, anti-microbial effect is achieved in body fluids such as plasma, serum or urine at concentrations less than about 0.5–1.5 µg/ml. Anti-microbial effect may be assessed for any particular coating or coating technique by measuring the zone of inhibition created when a portion of the coated device is placed on a bacterial lawn. One procedure for a zone of inhibition test is set out in the Examples which follow.

The ability to sustain release of metal ions from a coating is dictated by a number of factors, including coating characteristics such as composition, structure, solubility and thickness, and the nature of the environment in which the device is used. As the level of atomic disorder is increased, the amount of metal ions released per unit time increases. For instance, a silver metal film deposited by magnetron sputtering at T/Tm<0.5 and a working gas pressure of about 7 mTorr releases approximately ⅓ of the silver ions that a film deposited under similar conditions, but at 30 mTorr, will release over 10 days. Films that are created with an intermediate structure (ex. lower pressure, lower angle of incidence etc.) have Ag release values intermediate to these values as determined by bioassays. This then provides a method for producing controlled release metallic coatings in accordance with this invention. Slow release coatings are prepared such that the degree of disorder is low while fast release coatings are prepared such that the degree of disorder is high.

For continuous, uniform coatings, the time required for total dissolution will be a function of film thickness and the nature of the environment to which they are exposed. The relationship in respect of thickness is approximately linear, i.e. a two fold increase in film thickness will result in about a two fold increase in longevity.

It is also possible to control the metal release from a coating by forming a thin film coating with a modulated structure. For instance, a coating deposited by magnetron sputtering such that the working gas pressure was low (ex. 7 mTorr) for 50% of the deposition time and high (ex. 30 mTorr) for the remaining time, has a rapid initial release of metal ions, followed by a longer period of slow release. This type of coating is extremely effective on devices such as urinary catheters for which an initial rapid release is required to achieve immediate anti-microbial concentrations followed by a lower release rate to sustain the concentration of metal ions over a period of weeks.

Atomic disorder may also be achieved, in accordance with the present invention, by co- or sequentially depositing the anti-microbial metal(s) with one or more other inert, bicompatible metals selected from Ta, Ti, Nb, Zn, V, Hf, Mo, Si, Al and alloys of those metals or other transition metal elements. Such inert metals have a different atomic radii from that of the anti-microbial metals, which results in atomic disorder during deposition. Alloys of this kind can also serve to reduce atomic diffusion and thus stabilize the disordered structure. Thin film deposition equipment with multiple targets for the placement of each of the anti-microbial and inert metals is preferably utilized. The final ratio of the anti-microbial metal(s) to inert metal(s) should be greater than about 0.2. The most preferable inert metals are Ti, Ta and Nb. It is also possible to form the anti-microbial coating from oxides, carbides, nitrides etc. of one or more of the anti-microbial metals or one or more of the inert metals to achieve the desired atomic disorder.

Another deposition technique within the scope of the present invention is formed by reactively co- or sequentially depositing, by physical vapour techniques, a reacted material into the thin film of the anti-microbial metal(s). The reacted material is an oxide, nitride, carbide, boride, sulphide or halide of the anti-microbial or inert metal, formed in situ by injecting the appropriate reactant (ex. $O_2$, $N_2$, etc.) into the deposition chamber. The reactant may be continuously supplied during deposition for codeposition or it may be pulsed to provide for sequential deposition. The final ratio of anti-microbial metal(s) to reaction product should be greater than about 0.2.

The above deposition techniques may be used with our without the lower substrate temperatures, high working gas pressures and low angles of incidence previously discussed.

It may be advantageous, prior to depositing an anti-microbial in accordance with the present invention, to provide an adhesion layer on the device to be coated, as is known in the art. For instance, for a latex device, a layer of Ti, Ta or Nb may be first deposited to enhance adhesion of the subsequently deposited anti-microbial coating.

The invention is further illustrated by the following non-limiting examples.

EXAMPLE 1

A medical suture material size 2/0, polyester braid was coated by magnetron sputtering an Ag-Cu-alloy onto the surface to a thickness of 0.45 microns, using either argon gas working pressures of 7 mTorr or 30 mT at 0.5 KW power and a T/Tm ratio of less than 0.5.

The anti-microbial effect of the coatings was tested by a zone of inhibition test. Basal medium Eagle (BME) with Earle's salts and L-glutamine was modified with calf/serum (10%) and 1.5% agar prior to being dispensed (15 ml) into Petri dishes. The agar containing petri plates were allowed to surface dry prior to being inoculated with a lawn of

*Staphylococcus aureus* ATCC #25923. The inoculant was prepared from Bactrol Discs (Difco, M.) which were reconstituted as per the manufacturer's directions. Immediately after inoculation, the materials or coatings to be tested were placed on the surface of the agar. The dishes were incubated for 24 h at 37° C. After this incubation period, the zone of inhibition was measured and a corrected zone of inhibition was calculated (corrected zone of inhibition—zone of inhibition—diameter of the test material in contact with the agar).

The results showed no zone of inhibition on the uncoated suture, a zone of less than 0.5 mm around the suture coated at 7 mTorr and a zone of 13 mm around the suture coated at 30 mTorr. Clearly the suture coated in accordance with the present invention exhibits a much more pronounced and effective anti-microbial effect.

EXAMPLE 2

This example is included to illustrate the surface structures which are obtained when silver metal is deposited on silicon wafers using a magnetron sputtering facility and different working gas pressures and angles of incidence (i.e. the angle between the path of the sputtered atoms and the substrate). All other conditions were as follows: deposition rate was 200 A°/min; ratio of temperature of substrate (wafer) to melting point of silver (1234° K), T/Tm was less than 0.3. Argon gas pressures of 7 mTorr (a normal working pressure for metal coatings) and 30 mTorr were used. Angles of incidence at each of these pressures were 90° (normal incidence), 50° and 10°. The coatings had a thickness of about 0.5 microns.

The resulting surfaces were viewed by scanning electron microscope (SEM). As argon gas pressure increased from 7 to 30 mTorr the grain size decreased and the grain boundaries became more distinct. At 7 mTorr argon pressure and an angle of incidence of 10°, there were indications of some voids between the grains. The angle of incidence had a greater effect on the surface topography when the gas pressure was increased to 30 mTorr. At 90°, the grain size varied from 60–150 nm and many of the grains were separated by intergrain void spaces which were 15–30 nm wide. When the angle of incidence was decreased to 50°, the grain size decreased to 30–90 nm and the void volume increased substantially. AT 10°, the grain size was reduced to about 10–60 nm and void volumes were increased again.

The observed nanometer scale changes in surface morphology and topography are indications of atomic disorder in the silver metal. While not being bound by the same, it is believed that such atomic disorder results in an increase in the chemical activity due to increased internal stresses and surface roughness created by mismatched atoms. It is believed that the increased chemical activity is responsible for the increased level of solubility of the coatings when in contact with an electrolyte such as body fluid.

The anti-microbial effect of the coatings was evaluated using the zone of inhibition test as set out in Example 1. Each coated silicon wafer was placed on an individual plate. The results were compared to the zones of inhibition achieved when solid silver (i.e. greater than 99% silver) sheets, wires or membranes were tested. The results are summarized in Table 1. It is evident that the pure silver devices and the silver sputtered coating at 7 mTorr do not produce any biological effect. However, the coatings deposited at a higher than normal working gas pressure, 30 mTorr, demonstrated an anti-microbial effect, as denoted by the substantial zones of inhibition around the discs. Decreasing the angle of incidence had the greatest effect on antimicrobial activity when combined with the higher gas pressures.

TABLE I

Antimicrobial effects of various silver and silver coated samples as determined using *Staphylococcus aureus*

| Sample | Percent Silver | Angle of Deposition | Working Gas Pressure (mTorr) | Corrected Zone of Inhibition (mm) |
|---|---|---|---|---|
| Silver Sheet-rolled | 99+ | — | — | <0.5 |
| Silver wire (.0045") | 99+ | — | — | <0.5 |
| Silver membrane-cast | 99+ | — | — | <0.5 |
| Sputtered thin film | 99+ | normal (90°) | 7 | <0.5 |
| Sputtered thin film | 99+ | 50° | 7 | <0.5 |
| Sputtered thin film | 99+ | 10° | 7 | <0.5 |
| Sputtered thin film | 99+ | normal (90°) | 30 | 6.3 |
| Sputtered thin film | 99+ | 50° | 30 | 10 |
| Sputtered thin film | 99+ | 10 | 30 | 10 |

EXAMPLE 3

Silicon wafers were coated by magnetron sputtering with an alloy of Ag and Cu (80:20) at normal incidence at working gas pressures of 7 mTorr and 30 mTorr, all other conditions being identical to those set out in Example 2. As in Example 2, when the coatings were viewed by SEM, the coatings formed at high working gas pressure had smaller grain sizes and larger void volumes than die the coatings formed at the lower working gas pressures.

Coatings which were similarly formed from a 50:50 Ag/Cu alloy were tested for anti-microbial activity with the zone of inhibition test set out in Example 1. The results are summarized in Table 2. Coatings deposited at low working gas pressure (7 mTorr) showed minimal zones of inhibition, while the coatings deposited at high working gas pressure (30 mTorr) produced larger zones of inhibition, indicative of anti-microbial activity.

TABLE 2

The antimicrobial effect of various sputter deposited silver-copper alloys as determined using *Staphylococcus aureus*

| Sample | Percent Silver | Angle of Deposition (°) | Working Gas Pressure (mTorr) | Corrected Zone of Inhibition (mm) |
|---|---|---|---|---|
| 1 | 50 | normal (90°) | 7.5 | <0.5 |
| 2 | 50 | normal (90°) | 30 | 16 |
| 3 | 50 | 10 | 30 | 19 |

EXAMPLE 4

A coating in accordance with the present invention was tested to determine the concentration of silver ions released into solution over time. One $cm^2$ silicon wafer discs were coated with silver as set forth in Example 2 at 7 mTorr and 30 mTorr and normal incidence to a thickness of 5000 A°. Using the method of Nickel et al., Eur. J. Clin. Microbiol., 4(2), 213–218, 1985, a sterile synthetic urine was prepared and dispensed into test tubes (3.5 ml). The coated discs were placed into each test tube and incubated for various times at 37° C. After various periods of time, the discs were removed and the Ag content of the filtered synthetic urine was determined using neutron activation analysis.

The results are set forth in Table 3. The table shows the comparative amounts of Ag released over time from coatings deposited on discs at 7 mTorr or 30 mTorr. The coatings deposited at high pressure were more soluble than those deposited at low pressure. It should be noted that this test is a static test. Thus, silver levels build up over time, which would not be the case in body fluid where there is constant turn over.

TABLE 3

Concentration of silver (mg/ml) in synthetic urine as a function of exposure time

| Exposure Time (Days) | Working Argon gas pressure 7 mTorr | Working argon gas pressure 30 mTorr |
| --- | --- | --- |
| 0 | ND[1] | ND |
| 1 | 0.89 | 1.94 |
| 3 | 1.89 | 2.36 |
| 10 | 8.14 | 23.06 |

Note: Films were deposited at normal incidence (90°)
[1]ND (non detectable) <0.46 ug/ml

EXAMPLE 5

This example is included to illustrate coatings in accordance with the present invention formed from another noble metal, Pd. The coatings were formed on silicon wafers as set forth in Example 2, to a thickness of 5000 A°, using 7 mTorr or 30 mTorr working gas pressures and angles of incidence of 90° and 10°. The coated discs were evaluated for anti-microbial activity by the zone of inhibition test substantially as set forth in Example 1. The coated discs were placed coating side up such that the agar formed a 1 mm surface coating over the discs. The medium was allowed to solidify and surface dry, after which the bacterial lawn was spread over the surface. The dishes were incubated at 37° C. for 24 h. The amount of growth was then visually analyzed.

The results are set forth in Table 4. At high working gas pressures, the biological activity of the coating was much greater than that of coatings deposited at low pressure. Changing the angle of incidence (decreasing) improved the anti-microbial effect of the coating to a greater extent when the gas pressure was low than when it was high.

TABLE 4

Surface Control of *Staphylococcus aureus* by Sputter Deposited Palladium metal

| Sample | Sputtering Pressure | Angle of Deposition | Antimicrobial Control |
| --- | --- | --- | --- |
| 1 | 7 mT | 90° (normal incidence) | More than 90% of surface covered by bacterial growth |
| 2 | 7 mT | 10° (grazing incidence) | 20–40% of surface covered by bacterial growth |
| 3 | 30 mT | 90° (normal incidence) | Less than 10% surface covered by bacterial growth |

EXAMPLE 6

This example is included to illustrate the effect of silver deposition temperature on the antimicrobial activity of the coating. Silver metal was deposited on 2.5 cm sections of a latex Foley catheter using a magnetron sputtering facility. Operating conditions were as follows; the deposition rate was 200 A° per minute; the argon working gas pressure was 30 mTorr; and the ratio of temperature of substrate to melting point of the coating metal silver, T/Tm was 0.30 or 0.38. In this example the angles of incidence were variable since the substrate was round and rough. That is the angles of incidence varied around the circumference and, on a finer scale, across the sides and tops of the numerous surface features. The antimicrobial effect was tested by a zone of inhibition test as outlined in Example 1.

The results showed corrected zones of inhibition of 0.5 and 16 mm around the tubing coated at T/Tm values of 0.38 and 0.30 respectively. The sections of Foley catheter coated at the lower T/Tm value were more efficacious than those coated at higher T/Tm value The terms and expression in this specification are used as terms of description and not of limitation. There is no intention, in using such terms and expressions, of excluding equivalents of the features illustrated and described, it being recognized that the scope of the invention is defined and limited only by the claims which follow.

We claim:

1. A method for forming an anti-microbial coating on a medical device intended for use in contact with an alcohol or water based electrolyte, comprising:

depositing a coating containing one or more of the metals selected from the group consisting of Ag, Au, Pt, Pd, Hg, Sn, Cu, Sb, Bi and Zn or alloys of two or more of these metals on a surface of the medical device by physical vapor deposition to provide a thin film of the metal, in a crystalline form, having atomic disorder formed throughout the thickness of the film such that the coating, in contact with an alcohol or a water based electrolyte, provides a release of the metal ions at a concentration sufficient to provide a localized anti-microbial effect which is sufficient to generate a zone of inhibition of at least 6.3 mm s determined by incubating a coating on a bacterial lawn on a nutrient-containing agar medium and measuring the zone of clearing.

2. The method as set froth in claim 1 wherein the deposition is performed by vacuum evaporation, sputtering, magnetron sputtering or ion plating.

3. The method as set forth in claim 2, wherein the deposition is performed at a temperature such that a ratio of the temperature of the surface being coated to the melting point of the metal, in degrees Kelvin, is maintained at less than about 0.5.

4. The method as set forth in claims 2 or 3, wherein the deposition is performed such that an angle of incidence of coating flux on the medical device to be coated is less than about 75°.

5. The method as set forth in claims 2 or 3, wherein the deposition is performed by vacuum evaporation at a pressure greater than about 0.1 mT, by arc evaporation at a pressure greater than about 100 mT, or by pressure plating at a pressure greater than 200 mT.

6. The method as set forth in claims 2 or 3, wherein the deposition is performed by sputtering at a working gas pressure of greater than about 75 mT.

7. The method as set forth in claims 2 or 3, wherein the deposition is performed by ion plating at a working gas pressure of greater than about 10 mT.

8. The method as set forth in claims 2 or 3, wherein the deposition is performed by ion plating at a working gas pressure of greater than about 200 mT.

9. The method as set forth in claims 2 or 3, wherein the metal is selected from the group consisting of Ag, Au, Pt, Pd, Cu, and Zn or alloys of two or more of said materials.

10. The method as set forth in claims 2 or 3, wherein the metal is a noble metal or a noble metal alloy.

11. The method as set forth in claims 2 or 3, wherein the metal is Ag, Au or Pd or an alloy of these metals.

12. The method as set forth in claim 3, wherein the deposition is performed by magnetron sputtering at a working gas pressure of greater than about 30 mT.

13. The method as set forth in claim 3, wherein the metal is selected from Ag or Ag alloys.

14. A method of forming an anti-microbial coating on a medical device intended for use in contact with an alcohol or water based electrolyte, comprising:

depositing a coating containing one or more of the metals selected from the group consisting of Ag, Au, Pt, Pd, Hg, Sn, Cu, Sb, Bi and Zn or alloys of two or more of these metals on a surface of the medical device by physical vapor deposition conditions selected from vacuum evaporation at a pressure of greater than about 0.1 mT, arc evaporation at a pressure greater than about 100 mT, pressure plating at a pressure greater than 200 mT, sputtering at a working gas pressure of greater than about 75 mT, magnetron sputtering at a working gas pressure of greater than about 10 mT, or ion plating at a working gas pressure of greater than about 200 mT, to provide a thin film of the metal, in a crystalline form, having atomic disorder formed throughout the thickness of the film such that the coating, in contact with an alcohol or a water based electrolyte, provides a release of the metal ions at a concentration sufficient to provide a localized anti-microbial effect which is sufficient to generate a zone of inhibition of at least 6.3 mm as determined by incubating a coating on a bacterial lawn on a nutrient-containing agar medium and measuring the zone of clearing.

15. The method as set forth in claim 14, wherein the deposition is performed at a temperature such that a ratio of the temperature of the surface being coated to the melting point of the metal, in degrees Kelvin, is maintained at less than about 0.5.

16. The method as set forth in claim 15, wherein the deposition is performed such that an angle of incidence of coating flux on the medical device to be coated is less than about 75°.

17. The method as set forth in claim 15, wherein the metal is selected from the group consisting of Ag, Au, Pt, Pd, Cu, and Zn or alloys of two or more of said metals.

18. The method as set forth in claim 15, wherein the metal is a noble metal or a noble metal alloy.

19. The method as set forth in claim 15, wherein the metal is Ag, Au or Pd, or an alloy containing one or more of these metals.

20. The method as set forth in claim 15, wherein the deposition is performed by magnetron sputtering at a working gas pressure of greater than about 30 mT.

21. The method as set forth in claim 15, wherein the metal is selected from Ag or Ag alloys.

\* \* \* \* \*

UNITED STATES PATENT AND TRADEMARK OFFICE
CERTIFICATE OF CORRECTION

PATENT NO. :
DATED :
INVENTOR(S) :

5,770,255
June 23, 1998
Robert E. Burrell et al.

It is certified that error appears in the above-indentified patent and that said Letters Patent is hereby corrected as shown below:

Claim 1, col. 10, line 39, "s determined" should read -- as determined --.

Claim 2, col. 10, line 42, "froth" should read -- forth --.

Claim 7, col. 10, line 63, "ion plating" should read -- magnetron sputtering --.

Signed and Sealed this

Twenty-second Day of September, 1998

Attest:

BRUCE LEHMAN

*Attesting Officer*      *Commissioner of Patents and Trademarks*

UNITED STATES PATENT AND TRADEMARK OFFICE
CERTIFICATE OF CORRECTION

Page 1 of 2

PATENT NO. : 5,770,255
DATED : June 23, 1998
INVENTOR(S) : Robert E. Burrell, et. al.

It is certified that error appears in the above-identified patent and that said Letters Patent is hereby corrected as shown below:

| | | |
|---|---|---|
| In Col. 1, | Ln. 27, | change "mean" to -- meant --; |
| In Col. 2, | Ln. 16, | change "no" to -- not --; |
| | Ln. 28, | change "Tanemure" to -- Tanemura --; |
| In Col. 3, | Ln. 10, | change "interstisial" to -- interstitial --; |
| In Col. 4, | Ln. 19, | change "would" to -- wound --; |
| | Ln. 58, | change "dislocation" to -- dislocations --; |
| In Col. 5, | Ln. 11, | change "allows" to -- alloys --; |
| In Col. 6, | Ln. 16, | change "bicompatible" to -- biocompatible --; |
| | Ln. 17, | change "those" to -- these --; |
| | Ln. 44, | change "our" to -- or --; |
| | Ln. 66, | change "petri" to -- Petri --; |
| In Col. 7, | Ln. 8, | change "inhibition-zone" to -- inhibition = zone --; |
| | Ln. 9, | change "inhibition-diameter" to -- inhibition - diameter --; |
| | Ln. 35, | after "the grain size decreased and" insert -- void volume increased significantly. When the angle of incidence was decreased, the grain size decreased and --; |
| In Col. 8, | Ln. 37, | change "die" to -- did --; |
| In Col. 10, | Ln. 17, | change "value" to -- values. --; |
| | Ln.18, | change "expression" to -- expressions --; |
| In Col. 10, | Ln. 25, | change "for" to -- of --; |
| In Col. 11, | Ln. 3, | change "materials" to -- metals --. |

UNITED STATES PATENT AND TRADEMARK OFFICE
CERTIFICATE OF CORRECTION

PATENT NO. : 5,770,255
DATED : June 23, 1998
INVENTOR(S) : Robert E. Burrell, et. al.

It is certified that error appears in the above-identified patent and that said Letters Patent is hereby corrected as shown below:

Title page, item [56]
In References Cited:

| | | |
|---|---|---|
| On first Page, right Col., | Ln. 14, | delete "(no month)."; |
| | Lns. 18-19, | delete "(no month)."; |
| | Lns. 21-22, | delete "(no month)."; |
| | Ln. 25, | delete "(no month)."; |
| | Ln. 34, | delete "(no month)."; |
| | Ln. 40, | delete "(no month)."; |
| On second Page, right Col., | Ln. 13, | delete "no date available"; |
| | Ln. 29, | delete "(no month)."; |
| | Ln. 37, | delete "(no month)."; |
| | Ln. 45, | delete "(no month)."; |
| | Ln. 50, | delete "(no month)."; |
| | Ln. 54, | change "Reconstructuve" to -- Reconstructive--; |
| | Ln. 57, | delete "(no month)."; |
| | Ln. 60, | delete "(no month)."; |
| On third Page, left Col., | Ln. 4, | delete "(no month)."; |
| | Ln. 7, | delete "(no month)."; |
| | Ln. 10, | delete "(no month)."; |
| | Ln. 14, | delete "(no month)."; |
| On third Page, left Col., | Ln. 8, | delete "(no month)."; |
| | Ln. 13, | delete "(no month)."; |

Signed and Sealed this

Twelfth Day of September, 2000

Attest:

Q. TODD DICKINSON

*Attesting Officer*   *Director of Patents and Trademarks*